(12) United States Patent
Vertoprakhov

(10) Patent No.: US 7,292,331 B2
(45) Date of Patent: Nov. 6, 2007

(54) INSPECTION LIGHTING HEAD SYSTEM AND METHOD OF OPERATION

(75) Inventor: Victor Vertoprakhov, NovosiBirsk (RU)

(73) Assignee: Microview Technologies Pte Ltd, Singapore (SG)

( * ) Notice: Subject to any disclaimer, the term of this patent is extended or adjusted under 35 U.S.C. 154(b) by 264 days.

(21) Appl. No.: 11/080,004

(22) Filed: Mar. 15, 2005

(65) Prior Publication Data
US 2006/0209299 A1    Sep. 21, 2006

(51) Int. Cl.
*G01N 21/00* (2006.01)
(52) U.S. Cl. .................. 356/237.5; 356/237.1
(58) Field of Classification Search .. 356/237.1–237.5, 356/239.1–239.8, 317, 237.6; 250/231.13, 250/225; 359/642, 800, 801
See application file for complete search history.

(56) References Cited

U.S. PATENT DOCUMENTS

| | | | | |
|---|---|---|---|---|
| 5,177,559 A | * | 1/1993 | Batchelder et al. | ...... 356/237.5 |
| 6,006,119 A | * | 12/1999 | Soller et al. | ................. 600/322 |
| 6,177,954 B1 | * | 1/2001 | Bouvier | ........................ 348/92 |
| 6,330,059 B1 | * | 12/2001 | Ishiguro et al. | .......... 356/237.5 |
| 2004/0207836 A1 | * | 10/2004 | Chhibber et al. | ........ 356/237.4 |
| 2006/0033911 A1 | * | 2/2006 | Brown et al. | ................ 356/326 |
| 2006/0107211 A1 | * | 5/2006 | Mirtich et al. | .............. 715/700 |

* cited by examiner

*Primary Examiner*—Gregory J. Toatley, Jr.
*Assistant Examiner*—Tri Ton
(74) *Attorney, Agent, or Firm*—Jackson Walker L.L.P.; Christopher J. Rourk

(57) ABSTRACT

A system for high-speed inspection is provided. The system includes a digital camera focused on an inspection location and generating image data. An array of light emitting diodes generates light beams, and one or two lenses collimate the light beams. The angle of incidence of the collimated light on an item at the inspection location is greater than approximately 50 degrees, such as to avoid flashing which can be created by coating on the inspection item or other surface effects. The collimating lenses have a center hole and the digital camera is focused on the inspection location through the center hole.

20 Claims, 3 Drawing Sheets

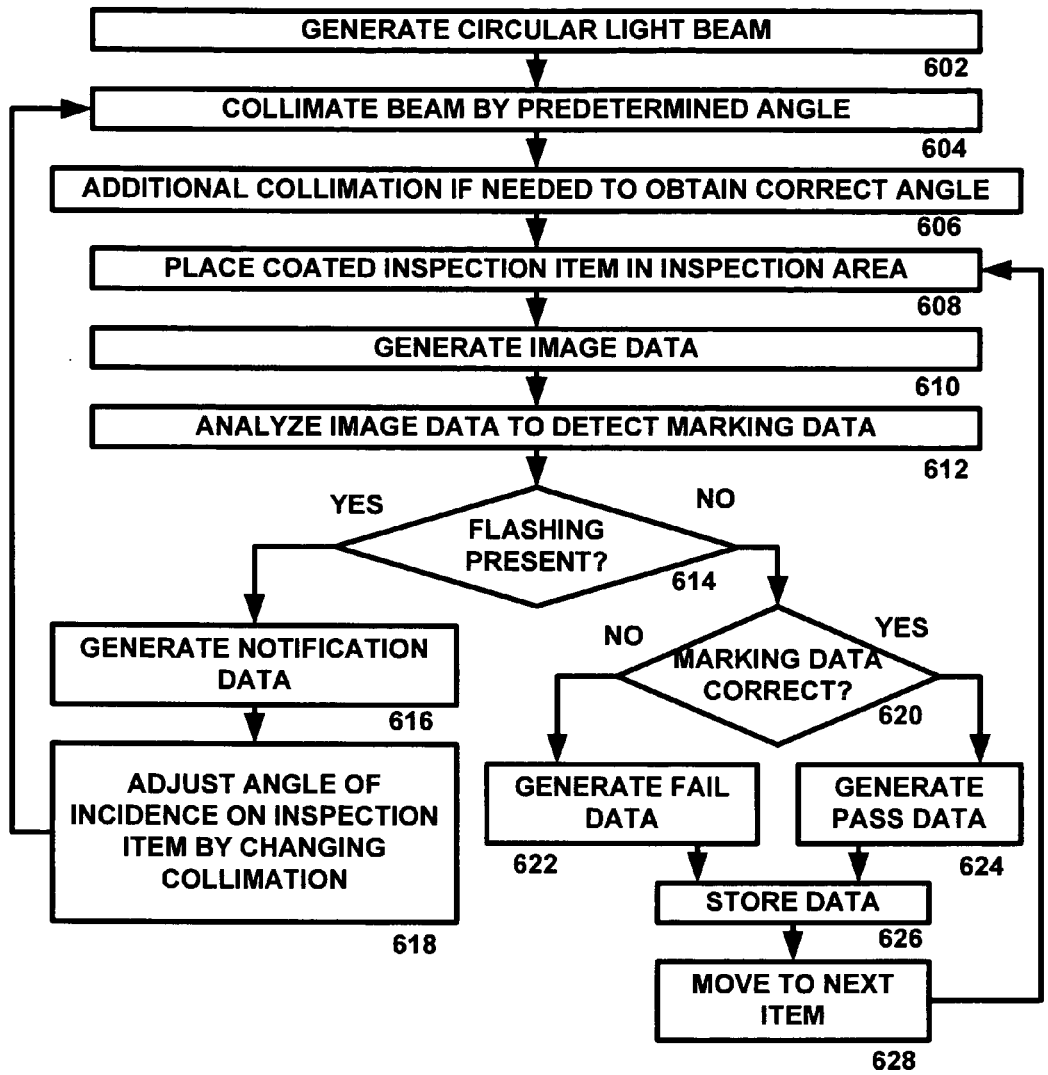
  600

INSPECTION LIGHTING HEAD SYSTEM AND METHOD OF OPERATION

FIELD OF THE INVENTION

The present invention relates to item inspection, and more specifically to a lighting head system and method that allows a high intensity beam of light to be directed to a small area at an angle of incidence that avoids flashing or other effects.

BACKGROUND

Item inspection systems are known in the art. Such systems typically use magnifiers to increase the effective resolution and decrease the effective picture element resolution area. Such magnification systems suffer from the drawback that magnification decreases light intensity, which requires more light to be directed to the inspection item. For a small inspection item, expensive items can be required to create sufficient light intensity. In addition, if the angle of incidence of the light is not controlled, flashing or other effects can occur due to coatings or other surface conditions of the inspection item that make it difficult or impossible to identify markings, defect indications, or other items of interest and for which the inspection is being performed.

SUMMARY OF THE INVENTION

In accordance with the present invention, an inspection lighting head is provided that overcomes known problems with inspection lighting heads.

In particular, an inspection lighting head and method of use are provided that allows a high intensity light beam to be directed onto a small area without the need for expensive lighting systems.

In accordance with an exemplary embodiment of the present invention, a system for high-speed inspection is provided. The system includes a digital camera focused on an inspection location and generating image data. An array of light emitting diodes generates a light beam, and a collimating lens receives the light beam from the array of light emitting diodes ("LEDs") and forms collimated light. A second collimating lens can also be used where necessary to obtain a desired angle of incidence on the inspection location. The angle of incidence of the collimated light on an item 110 at the inspection location is greater than approximately 50 degrees, such as to avoid flashing which can be created by coating on the inspection item or other surface effects.

The present invention provides many important technical advantages. One important technical advantage of the present invention is a system for increasing the intensity of light that is provided to a small inspection area while controlling the collimating of the light.

Those skilled in the art will further appreciate the advantages and superior features of the invention together with other important aspects thereof on reading the detailed description that follows in conjunction with the drawings.

DETAILED DESCRIPTION OF PREFERRED EMBODIMENTS

Figure 1:
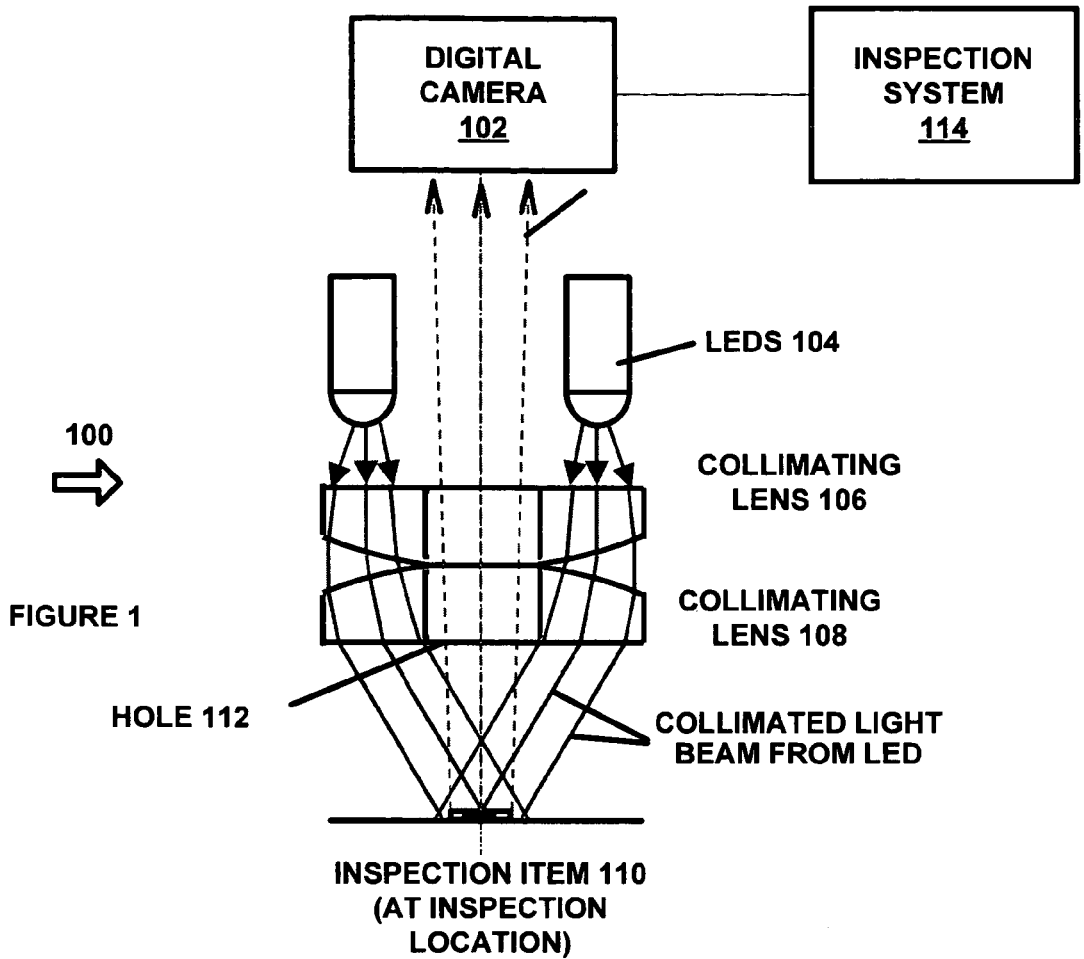
FIG. 1 is a diagram of a system for focusing a light beam on an inspection item in accordance with an exemplary embodiment of the present invention.

In the description that follows, like parts are marked throughout the specification and drawings with the same reference numerals, respectively. The drawing figures might not be to scale, and certain items can be shown in generalized or schematic form and identified by commercial designations in the interest of clarity and conciseness.

FIG. 1 is a diagram of a system 100 for focusing a light beam on an inspection item 110 in accordance with an exemplary embodiment of the present invention. System 100 allows light from a light source such as LEDs to be collimated so as to illuminate an inspection item having a coated surface or other surface features at an angle of incidence that reduces the amount of flashing, such as reflections from the coated surface that can interfere with an inspection of the item.

System 100 includes digital camera 102, which includes a sensor array and an imaging objective that increases the magnification factor of the image. In one exemplary embodiment, digital camera 102 can be used to inspect items having a very small size, such as less than 1 millimeter in diameter. For such items, to perform a high speed inspection it may be necessary to highly illuminate the item in order to magnify the image of the item by a sufficient amount to read characters on the item. Digital camera 102 allows high speed inspection of a small item to occur, but typically requires that the item be illuminated with a high degree of intensity of light so as to generate sufficient image data for inspection to occur.

Inspection system 114 is coupled to digital camera 102. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections. In one exemplary embodiment, systems and components are coupled to other systems and components through intervening systems and components, such as through an operating system. Communications media can be a local area network, a wide area network, a public network such as the Internet, the public switched telephone network, a wireless network, a fiber optic network, other suitable media, or a suitable combination of such media.

Inspection system 114 can be implemented in hardware, software, or a suitable combination of hardware and software, and can be one or more software systems operating on a general purpose processing platform. As used herein, a hardware system can include discrete semiconductor devices, an application-specific integrated circuit, a field programmable gate array, a general purpose processing platform, or other suitable devices. A software system can include one or more objects, agents, threads, lines of code, subroutines, separate software applications, user-readable (source) code, machine-readable (object) code, two or more lines of code in two or more corresponding software applications, databases, or other suitable software architectures. In one exemplary embodiment, a software system can include one or more lines of code in a general purpose software application, such as an operating system, and one or more lines of code in a specific purpose software application.

Inspection system 114 receives image data from digital camera 102 and determines if character data can be recognized from the inspection image data of an inspection item 110. In one exemplary embodiment, inspection system 114 can generate notification data if the amount of flashing or other artifacts being generated are hindering or preventing inspection of items, can generate data that causes collimating lens 106 and collimating lens 108 to be changed out manually or automatically, can generate operator notification data to change out such lenses, can receive item type data and select collimating lens 106 and collimating lens 108 based on the type of item, or can perform other suitable functions.

LEDs 104 are an array of light emitting diodes that generate light in a circular array or another suitable formations. Collimating lens 106 and collimating lens 108 collimate the light from LEDs 104 so that the collimated conical ring-shaped light beam falls onto an inspection site at a pre-determined angle of incidence. For example, it has been observed that the angle of incidence for small items with coated surfaces should be equal to or greater than 50 degrees to avoid flashing. Light from inspection item 110 is reflected and is scattered through hole 112 to digital camera 102.

System 100 allows conventional light sources such as LEDS to be used to illuminate small items that may be covered with a coating or have other surface features that require the angle of incidence of the light illuminating an item to be controlled. System 100 thus allows high speed inspection of small items to be performed, such as where the image data from the item must be magnified by a significant magnification factor in order to allow the image data to be analyzed to inspect the item.

Figure 2:
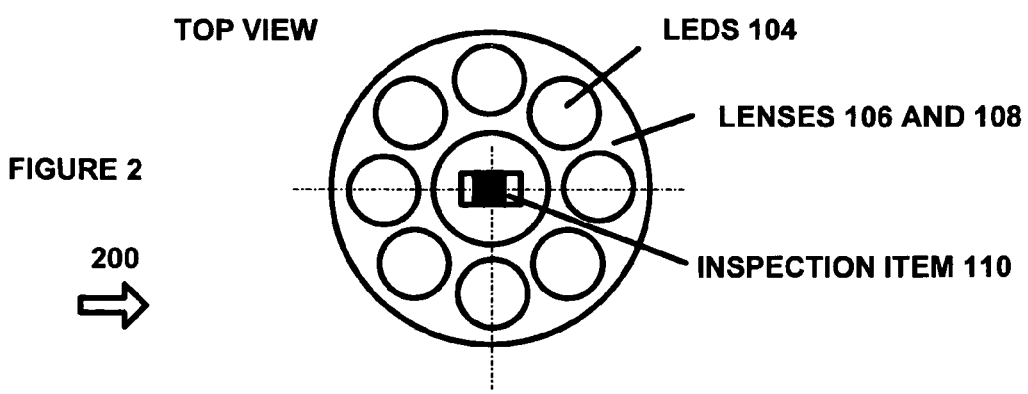
FIG. 2 is a top view of an LED array and inspection item in accordance with an exemplary embodiment of the first invention.

FIG. 2 is a top view 200 of an LED array and inspection item 110 in accordance with an exemplary embodiment of the first invention. FIG. 2 shows a circular array of LEDs 104 over lenses 106 and 108. Likewise, hole 112 allows inspection item 110 to be seen through the LED array. In one exemplary embodiment, hole 112 is less than several millimeters in diameter and inspection item 110 is less than one millimeter in size. As a result of the small sizes of hole 112 and inspection item 110, a high degree of magnification can be required in order to generate image data to perform inspection of inspection item 110.

Figure 3:
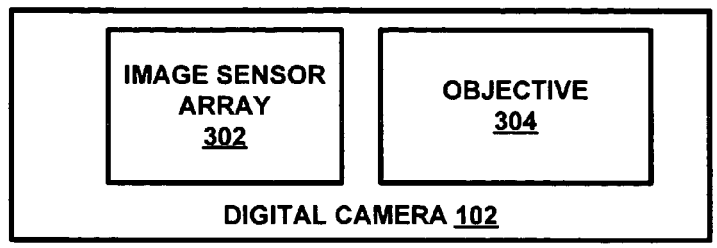
FIG. 3 is the diagram of an digital camera in accordance with an exemplary embodiment of the present invention.

FIG. 3 is the diagram of a digital camera assembly 300 in accordance with an exemplary embodiment of the present invention. Digital camera assembly 300 includes digital camera 102, image sensor array 302 and objective 304.

Image sensor array 302 can be a suitable array of CMOS or other image sensing devices that create an N×M array of picture elements, where N and M are integers. In one exemplary embodiment, image sensor array 302 can have a response time that is based on the amount of light that is collected by each picture element, such that to increase the speed of digital image generation, it is necessary to ensure that sufficient photons of light energy are received at each picture element to generate image data at that picture element.

Objective 304 allows the magnification factor applied to light that is impinged on image sensor array 302 to be altered, such as to accommodate different inspection item sizes or for other suitable purposes. In one exemplary embodiment, as a objective's magnification factor increases three times, the amount of light received at image sensor array 302 decreases nine times accordingly at other things being equal, such that in order to keep the speed of digital image sensor array 302 constant, it would be necessary to increase the intensity of light on the inspection item up to nine times.

In operation, system 300 allows an image sensor array to receive light and generate digital image data for inspection of an item. Objective 304 allows the magnification factor to be adjusted so as to optimize the amount of magnification for a given item.

Figure 4:
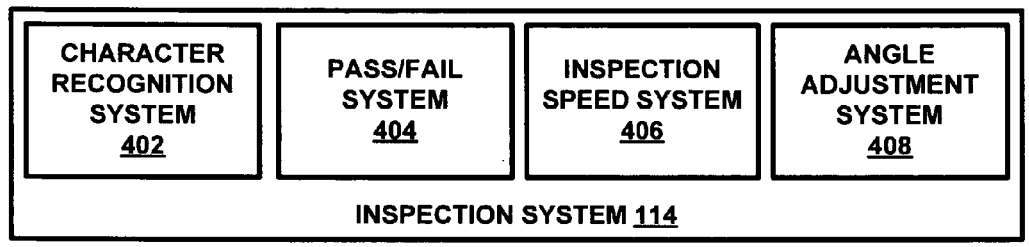
FIG. 4 is a diagram of a system for performing an inspection in accordance with an exemplary embodiment of the present invention.

FIG. 4 is a diagram of a system 400 for performing an inspection in accordance with an exemplary embodiment of the present invention. System 400 includes inspection system 114 and character recognition system 402, pass/fail system 404, inspection speed system 406, and angle adjustment system 408, each of which can be implemented in hardware, software, or a suitable combination of hardware and software, and which can be one or more software systems operating on a general purpose processing platform.

Character recognition system 402 receives a set of image data of an item and determines whether one or more characters are present in the set of image data. In one exemplary embodiment, character recognition system can use character matching based on predetermined item types that are being inspected, can look for defects or other image data, can compare characters based on histogram data for sectors of the image data, or can perform other suitable functions.

Pass/fail system 404 receives a set of image data from digital camera 102 or character recognition system 402 and determines whether the item being inspected has passed or failed inspection. In one exemplary embodiment, pass/fail system 404 can receive a set of characters that are expected to be present on the item being inspected, and can determine whether character recognition system 402 has returned that set. In another exemplary embodiment, pass/fail system 404 can determine the size of defects, whether detected defects from character recognition system 402 fall within permitted bounds for allowable defects, or other suitable data. Likewise, pass/fail system 404 can generate operator notification data so that the operator can stop the item inspection process and correct the test data to match the items being inspected, pass/fail system 404 can generate index data to identify the location of an item or inspection item that has failed inspection, or can perform other suitable functions.

Inspection speed system 406 receives character data from character recognition system 402 and determines whether the inspection speed can be increased or decreased. In one exemplary embodiment, if character recognition system 402 is generating data that indicates that characters are not being recognized due to insufficient lighting, inspection speed system 406 can generate inspection speed controls that reduce the speed of the inspection, so as to increase the amount of time that each inspection item is illuminated. In this manner, the amount of light energy transmitted to image sensor array 302 can be increased, which can increase the ability of character recognition system 402 to identify characters in the set of image data. Likewise, if character recognition system 402 is generating image data that does not indicate any problems with a lack of light from the inspection item, inspection speed system 406 can increase the inspection speed to a point where the inspection time is optimized.

Angle adjustment system 408 receives image data from character recognition system 402 and pass/fail system 404 and determines whether the angle of incidence on an inspection item is creating flashing or other artifacts. Angle adjustment system 408 can generate operator notification data to replace one or more of the collimating lens 106 and collimating lens 108, can automatically select appropriate collimating lens 106 and collimating lens 108 and install them in the inspection apparatus, or can perform other suitable functions.

In operation, system 400 allows items to be inspected that are small in size and are being subjected to high magnification factors. System 400 can be used where the small items have characters or other markings that need to be recognized and also allows the speed of the inspection process to be adjusted based on the amount of light, can generate operator notification data in the event of flashing or other problems caused by an improper angle of incidence, and can perform other suitable functions.

Figure 5:
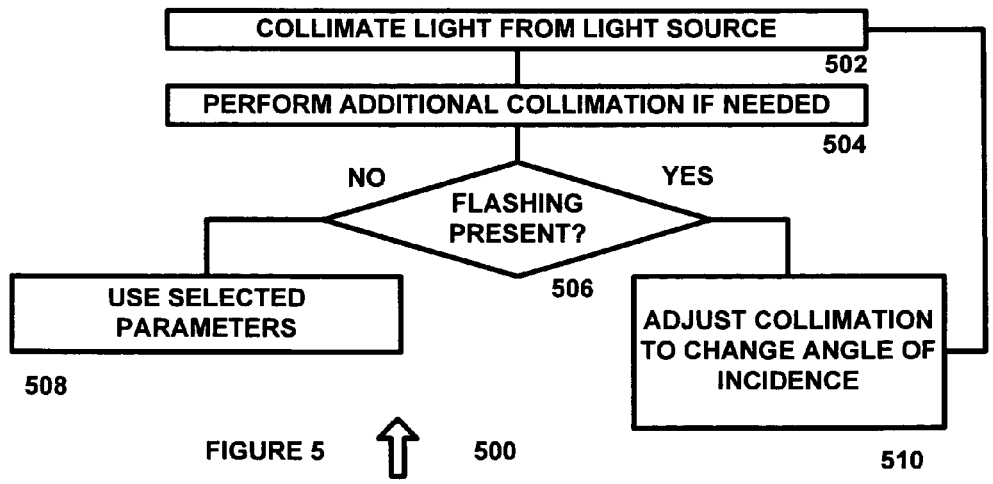
FIG. 5 is a flow chart of a method for inspecting coated items in accordance with an exemplary embodiment of the present invention.

FIG. 5 is a flow chart of a method 500 for inspecting coated items in accordance with an exemplary embodiment of the present invention. Method 500 is used for small items subject to high magnification factors, such as where the flashing from a coating of the item can obscure the image.

At 502 light from a light source is collimated as conical ring-shaped light beam which falls onto an inspection site at pre-determined an angle of incidence. In one exemplary embodiment, a lens having a pre-determined collimating angle can be used. The method then proceeds to 504 where light from the light source that has been collimated is further collimated. In one exemplary embodiment, a parameters of collimating lenses 106 & 108 (focal length, distance between the lenses, and distances to LEDs and to inspection location) can be changed to achieve desirable angle of incidence of light on inspection area. The method then proceeds to 506.

At 506 it is determined whether flashing is present. In one exemplary embodiment, flashing can occur based on the geometric dimensions of the item being inspected, the coating qualities, the angle of incidence of the light, or other such variables. If it is determined at 506 that flashing is present, then the method proceeds to 510 where the cone angle is adjusted to change the angle of incidence. In one exemplary embodiment, the cone angle can be adjusted by changing lens sets to adjust the angle of incidence, a light source such as a fiber optic light source having a controlled angle incidence can be used to determine the proper angle of incidence and collimating lenses can be selected based upon that angle of incidence or other suitable processes can be used. The method then returns to 502.

If it is determined at 506 that flashing is not present the method proceeds to 508 and the selected parameters are used for performing inspection of that item. As previously noted, the angle of incidence can vary as a function item, such that each item can be associated with a different collimating lens set.

In operation, method 500 allows small items, such as those that have coated surfaces or other surface features that make inspection difficult, to be inspected at high speed, such as by determining whether flashing is present at levels of illumination that are required to generate image data of the item at high speed. Method 500 allows the angle of incidence required for different items to be determined and indexed such that the correct angle of incidence can be used for a given item.

Figure 6:
FIG. 6 is a flow chart of a method for inspecting items in accordance with exemplary embodiment of the present invention.

FIG. 6 is a flow chart of a method 600 for inspecting items in accordance with exemplary embodiment of the present invention. Method 600 begins at 602 where a circular light beam is generated. In one exemplary embodiment, a circular light beam can be generated by a circular array of LEDs or other conventional and inexpensive light generating sources. In this manner, expensive or special designed light sources can be avoided. Likewise, other suitable configurations of light beams can be generated, such as oblong, square, point, or other suitable light beams. The method then proceeds to 604.

At 604 the circular light beam is collimated as conical ring-shaped light beam with a pre-determined cone angle. The angle of collimation can be determined based upon coordination of the collimation with a subsequent collimation stage. The method then proceeds to 606.

At 606 the collimated light beam is further collimated by a predetermined angle. Likewise, a single stage of collimation can be used where suitable. The method then proceeds to 608.

At 608 a coated inspection item is placed in an inspection area. In one exemplary embodiment, the coated inspection item can be an item having small dimensions, such as less than 1 millimeter in diameter, and can receive high levels of illumination in order to perform high speed inspection. In this exemplary embodiment, the inspection item can be placed in the inspection area based on movement by conveyor, robot arm, movement of the image sensor array, or in other suitable manners. The method then proceeds to 610.

At 610 image data of the item is generated. In one exemplary embodiment, an image sensor array with a imaging objective can be used to generate the image data. The generation of image data is based on the amount of light energy received at each picture element over a period of time, such that the exposure time required to generate the image data is a function of the amount of light received. Since image magnification of a small item results in decreasing the amount of light received from the item, image generation speed can be increased by increasing the amount of light provided to the item, as long as such lighting does not result in flashing or other unacceptable artifacts. The method then proceeds to 612.

At 612 the image data is analyzed to detect marking data on the image, such as characters, defects, or other markings. The method then proceeds to 614.

At 614 it is determined whether flashing or other artifacts are present. In one exemplary embodiment, flashing can be determined to be present when image recognition is not possible, based upon histogram data that is characteristic of flashing or other artifacts, or in other suitable manners. If it is determined that flashing is present, the method proceeds to 616 where notification data is generated, such as an operator message, or instruction data for withdrawal and adjustment of an angle of incidence, such as by selecting alternate collimating lenses. The method then proceeds to 618.

At 618 the angle of incidence on the inspection item is changed by changing parameters of one or more collimating lenses. In one exemplary embodiment, the collimating lenses can be automatically selected, such as by robotic assembly, and replaced, a collimating lens set identifier can be provided to an operator for correction, such as where the operator has selected the wrong collimating lens set for a given set of items that are being inspected, or other suitable processes can be used. The method then returns to 604.

If it is determined at 614 that flashing or other artifacts are not present the method proceeds to 620 where it is determined whether the marking data is correct. As previously described, the marking data can be characters that are present or that are expected to be present on the surface of the inspection item, can be defects, or other suitable markings. If the marking data is correct (e.g., if the expected characters are present or if no defects are detected), the method proceeds to 624 and pass data is generated. Otherwise, the method proceeds to 622 where fail data is generated. From 622 the method proceeds to 626 where the data is stored. In one exemplary embodiment, the data can be indexed so that the failed item can be removed after a tray, array, tube, or other set of inspection items has been inspected. Likewise, operator notification data can be generated if the failure data indicates that an improper item type has been selected such that improper inspection procedures are being used for the item. The method then proceeds to 628 where the next item to be inspected is brought into the inspection area and the method returns to 608.

In operation, method 600 allows items to be inspected, such as small items with surface coatings that can create flashing and that require light to be provided at high intensities and at pre-determined angles of incidence. Method 600 thus allows small items to be inspected at high speeds without flashing effects resulting in erroneous inspection failure data.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A system for high-speed inspection comprising:
    a digital camera focused on an inspection location and generating image data;
    an array of light emitting diodes;
    a collimating lens receiving the array of light emitting diodes and collimating the light on the inspection location; and
    wherein the angle of incidence of the collimated light on an item at the inspection location is greater than approximately 50 degrees, and the collimating lens has a top, a bottom, and a circular perimeter and the array of light emitting diodes is a circular array that is disposed around a circumference of the collimating lens.

2. The system of claim 1 wherein the collimating lens further comprises one or more additional collimating lenses to obtain a desired angle of incidence of the collimated light.

3. The system of claim 1 wherein the collimating lens has a center hole and the camera is focused on the inspection location through the center hole.

4. The system of claim 1 wherein the camera applies a high optical magnification factor, and the collimated light increases the light intensity on the inspection location to allow the exposure time required for the camera to capture an image to be decreased.

5. The system of claim 1 further comprising an inspection item having a compound surface, wherein the angle of incidence of the collimated light is selected to prevent flashing from the compound surface.

6. The system of claim 1 wherein the inspection location is circular having a diameter smaller than 1 mm.

7. The system of claim 1 further comprising an inspection system receiving the image data and identifying one or more markings on a surface of an inspection item underneath a coating compound.

8. The system of claim 1 further comprising:
    a character recognition system receiving the image data and identifying one or more characters on a surface of an inspection item underneath a coating compound; and
    a pass/fail system generating pass/fail data for the inspection item based on the one or more characters.

9. The system of claim 1 further comprising a character recognition system receiving the image data and identifying one or more characters on a surface of an inspection item underneath a coating compound.

10. A system for high-speed inspection comprising:
    a high-speed digital camera with a high optical magnification factor focused on a circular inspection location having a diameter of less than 1 mm;
    a circular array of light emitting diodes;
    a circular collimating lens having a top, a bottom, and a hole at the center, wherein the circular array of light emitting diodes is disposed at the top of and around a circumference of the circular collimating lens, the circular collimating lens receiving light from the array of light emitting diodes and emitting collimated light;
    an inspection item having a compound on a surface of the inspection item, the inspection item disposed at the inspection location; and
    wherein the high-speed digital camera is focused on the inspection item through the hole of the collimating lens, and where an angle of incidence of the collimated light on an item at the inspection location is selected to mitigate flashing caused by the compound on the surface of the inspection item, the angle of incidence being greater than approximately 50 degrees.

11. A method for inspecting an item comprising:
    generating a ring-shaped light beam;
    collimating the ring-shaped light beam so as to direct the collimated, conical ring-shaped light beam onto an inspection site at an angle of incidence greater than approximately 50 degrees so as to mitigate flashing from an inspection item having a surface coated with a compound.

12. The method of claim 11 further comprising generating digital image data of the inspection item at a high speed and using a high magnification ratio, wherein the collimated, conical ring-shaped light beam reduces an expose time required to generate the digital image data of the inspection item by increasing a light intensity on the inspection item.

13. The method of claim 11 wherein generating the ring-shaped light beam comprises generating the ring-shaped light beam from an array of light emitting diodes.

14. The method of claim 11 wherein collimating the circular light beam comprises:
    determining an angle of incidence that will provide the circular light beam to a second collimating lens at a predetermined angle so as to provide the collimated, conical light beam onto an inspection site at an angle of incidence greater than approximately 50 degrees; and
    providing the second collimating lens between the circular light beam and the inspection item that collimates the circular light beam at the predetermined angle of incidence.

15. The method of claim 11 wherein collimating the circular light beam comprises:

determining an angle of collimation that will provide the collimated, conical light beam onto an inspection site at an angle of incidence greater than approximately 50 degrees; and providing a second collimating lens between the circular light beam and the inspection item that collimates the circular light beam at the predetermined angle of collimation.

16. The method of claim 11 further comprising:

generating digital image data of the inspection item at a high speed; and detecting alphanumeric data from the surface of the inspection item underneath the compound in the digital image data.

17. The method of claim 11 further comprising:

generating digital image data of the inspection item at a high speed using a high-speed digital camera with a high optical magnification factor; and detecting marking data from the inspection item in the digital image data.

18. The method of claim 11 wherein a tip of the conical ring-shaped light beam has a diameter smaller than 1 mm.

19. The method of claim 11 further comprising:

generating digital image data of the inspection item at a high speed using a high-speed digital camera with a high optical magnification factor; detecting marking data from the inspection item in the digital image data; and generating notification data if the marking data does not match predetermined marking data.

20. The method of claim 11 further comprising:

generating digital image data of the inspection item at a high speed using a high-speed digital camera with a high optical magnification factor; and detecting alphanumeric data from the inspection item in the digital image data.

* * * * *

UNITED STATES PATENT AND TRADEMARK OFFICE
CERTIFICATE OF CORRECTION

PATENT NO. : 7,292,331 B2
APPLICATION NO. : 11/080004
DATED : November 6, 2007
INVENTOR(S) : Victor Vertoprakhov It is certified that error appears in the above-identified patent and that said Letters Patent is hereby corrected as shown below:

Col. 7, line 41, after "receiving" please insert -- light from --;

Col. 7, line 44, please change "the" (first occurrence) to -- an --;

Col. 7, line 55, before "camera" please insert -- digital --;

Col. 7, line 57, before "camera" please insert -- digital --;

Col. 7, line 59, please change "the" (first occurrence) to -- a --;

Col. 7, line 60, please change "the" (first occurrence) to -- an -- , and before "camera" please insert -- digital --;

Col. 8, line 39, please change "the" (second occurrence) to -- a --;

Col. 8, line 56, please change "circular" to -- ring-shaped --;

Col. 8, line 58, please change "circular" to -- ring-shaped --;

Col. 8, lines 62 and 63, please change "circular" to -- ring-shaped --;

Cot. 8, line 67, please change "circular" to -- ring-shaped --;

Col. 9, line 5, please change "circular" to -- ring-shaped --;

UNITED STATES PATENT AND TRADEMARK OFFICE
CERTIFICATE OF CORRECTION

PATENT NO. : 7,292,331 B2
APPLICATION NO. : 11/080004
DATED : November 6, 2007
INVENTOR(S) : Victor Vertoprakhov It is certified that error appears in the above-identified patent and that said Letters Patent is hereby corrected as shown below:

Col. 9, line 7, please change "circular" to -- ring-shaped --.

Signed and Sealed this

Twenty-sixth Day of May, 2009

JOHN DOLL
*Acting Director of the United States Patent and Trademark Office*